United States Patent [19]

Park

[11] Patent Number: 5,389,359

[45] Date of Patent: Feb. 14, 1995

[54] PHARMACEUTICAL PREPARATION CONTAINING L-ASPARTATE OR L-ASPARAGINE FOR PREVENTING ETHANOL TOXICITY, AND PROCESS FOR PREPARATION THEREOF

[75] Inventor: Sang C. Park, Seoul, Rep. of Korea

[73] Assignee: Miwon Co., Ltd., Seoul, Rep. of Korea

[21] Appl. No.: 182,506

[22] Filed: Jan. 18, 1994

[30] Foreign Application Priority Data

Jun. 28, 1993 [KR] Rep. of Korea ............... 93-11849
Dec. 3, 1993 [KR] Rep. of Korea ............... 93-26324

[51] Int. Cl.$^6$ ............... A61K 31/045; A61K 31/195
[52] U.S. Cl. ............................................. 424/10; 424/2;
424/406; 514/557; 514/578; 514/724; 514/811;
514/974; 426/75; 426/590; 426/592; 426/599
[58] Field of Search ............. 514/811, 974, 557–578,
514/724; 424/2, 10, 406; 426/75, 590–599

[56] References Cited

U.S. PATENT DOCUMENTS

| | | | |
|---|---|---|---|
| 3,009,859 | 11/1961 | Laborit | 167/65 |
| 3,876,783 | 4/1975 | Gavrilescu et al. | 424/247 |
| 4,038,421 | 7/1977 | Mendy et al. | 426/72 |
| 4,479,974 | 10/1984 | Schenz | 426/590 |
| 4,593,020 | 6/1986 | Guinot | 514/811 |
| 4,703,045 | 10/1987 | Guinot | 514/811 |
| 4,738,856 | 4/1988 | Clark | 426/74 |
| 4,870,057 | 9/1989 | Chiapparelli et al. | 514/811 |
| 4,913,923 | 4/1990 | Van Den Ouweland | 426/533 |
| 4,992,282 | 2/1991 | Mehansho et al. | 426/72 |
| 4,997,672 | 3/1991 | DeSimone et al. | 426/649 |
| 5,102,910 | 4/1992 | Mittheiss et al. | 514/494 |
| 5,145,707 | 9/1992 | Lee | 426/649 |
| 5,176,934 | 1/1993 | Lee | 426/549 |
| 5,324,516 | 6/1994 | Pek et al. | 514/811 |

FOREIGN PATENT DOCUMENTS

| | | |
|---|---|---|
| 2208576 | 10/1972 | Germany. |
| 949076 | 2/1964 | United Kingdom. |
| 1066084 | 4/1967 | United Kingdom. |
| 1068478 | 5/1967 | United Kingdom. |
| 1508662 | 4/1978 | United Kingdom. |
| 89/04165 | 5/1989 | WIPO. |
| 91/16909 | 11/1991 | WIPO. |

OTHER PUBLICATIONS

Crownover et al, The Journal of Pharmacology and Experimental Therapeutics, vol. 236, No. 3, pp. 574–579 (1985).
Scholz et al, Eur. J. Biochem., vol. 63, pp. 449–458 (1976).
Ylikahri et al, Metabolism, vol. 20, No. 6, pp. 555–567 (1971).
Berry et al, Eur. J. Biochem., vol. 89, pp. 237–241 (1978).
Lister et al, TINS, vol. 10, No. 6, pp. 223–225 (1987).
Suzdak et al, Science, vol. 234, pp. 1243–1246 (1986).
Corda et al, European Journal of Pharmacology, vol. 159, pp. 233–239 (1989).
Judd et al, Am. J. Psychiatry, vol. 141, No. 12, pp. 1517–1521 (1984).
Mezey, Biochemical Pharmacology, vol. 25, pp. 869–875 (1976).
Nuotto et al, Clin. Pharmacol. Ther., vol. 31, No. 1, pp. 68–76 (1981).
Menon et al, Life Sciences, vol. 37, pp. 2091–2098 (1985).
Alkana et al, Psychopharmacology, vol. 77, pp. 11–16 (1982).
Alkana et al, Psychopharmacology, vol. 55, pp. 203–212 (1977).
Gianoulakis, Experientia, vol. 45, pp. 428–435 (1989).

(List continued on next page.)

Primary Examiner—Shep K. Rose
Attorney, Agent, or Firm—Birch, Stewart, Kolasch & Birch

[57] ABSTRACT

Compositions containing L-aspartate or L-asparagine for use as additives to foods, soft drinks, vitamins, and the like are described. A method for preventing ethanol toxicity in a human subject is also provided.

6 Claims, 4 Drawing Sheets

OTHER PUBLICATIONS

Hoek et al, The FASEB Journal, vol. 6, pp. 2386–2396 (1992).

Mitchell et al, Ann. Rev. Nutr., vol. 6, pp. 457–474 (1986).

Gullans et al WO/PCT 91/14435 (Oct. 3, 1991) GA. 115: 248120w.

Knight JPN 03052 810 (Mar. 7, 1991) GA. 115: 214851v.

Mudzhiri et al U.K. 2 198041 (Jun. 8, 1988) GA. 111: 72962y.

Brekhman et al Ger DE 3641495 (Jun. 9, 1988) GA. 110: 121412j.

Gavrilescu et al Embase Abstract of Agressologie (16/4): 253–356 (1975).

Poey et al Medline Abstract of Toxicol. Eur. Res. 1(5): 303–9 (1978).

Boucharlat et al. Medline Abstract of Ann Med Psychol 1(3): 394–400 Mar. 1992.

PHARMACEUTICAL PREPARATION CONTAINING L-ASPARTATE OR L-ASPARAGINE FOR PREVENTING ETHANOL TOXICITY, AND PROCESS FOR PREPARATION THEREOF

BACKGROUND OF THE INVENTION

1. Field of the Invention

The present invention relates to a pharmaceutical preparation comprising L-aspartate (hereinafter "ASP") or L-asparagine (hereinafter "ASN") and a process for the preparation thereof. More particularly, the invention relates to a pharmaceutical composition of ASP or ASN for use in adding to foods, food additives, soft drinks, vitamins, an ASP compound or an ASN compound, a method of administering about 0.001–0.4 g/Kg/day of ASP or ASN to a human for preventing ethanol toxicity, and a process for the preparation of such compositions.

2. Description of Related Art

Both ASP and ASN have been obtained from natural substances or synthetic methods. It has been previously disclosed in the art that such ASP or ASN is widely used as a food additive, being added in small amounts. However, ASP or ASN is unknown to prevent ethanol toxicity by administering a large amount thereof to a human.

There have been suggestions of means for stimulating ethanol oxidation or blocking the cellular toxicity of ethanol. For example, fructose has long been suggested to have the potential to stimulate ethanol oxidation by the following mechanism: fructose is first converted to fructose 1-phosphate via the action of fructokinase with the simultaneous conversion of ATP to ADP, which is transported into the mitochondria, where it stimulates oxygen uptake and the reoxidation of NADH (Crownover et al., 1986, Scholz & Nohl 1976, Ylikari et al. 1971). But as to the efficiency of the fructose effect on ethanol oxidation, there is still dispute (Berry & Kun 1978).

In another instance, an imidazodiazepine compound R015-4513 (ethyl 8-azido-5,6-dihydro-5-methyl-6-oxo-4H-imidazo[1,5-1][1,4]benzodiazepine-3-carboxylate) has been reported to function as a specific alcohol antagonist (Lister & Nutt 1987, Hoffman et al. 1987). The specific biochemical role of R015-4513 was noticed from its activity in reversing ethanol's stimulatory effect on GABA-mediated Cl− flux in synaptosomes (Suzdak et al. 1986). A curative effect on ethanol-induced behavioral derangements has been observed for R015-4513. However, the toxic effects of R015-4513 still limit its general application (Corda et al. 1989). In addition, GABA antagonists, serotonin uptake inhibitors, α-adrenoceptor antagonists, lithium, caffeine, Thyroid Hormone Releasing Hormone (TRH) and hyperbaric oxygen have been reported to have the potential to reverse (at least in part) some of the behavioral effects of ethanol (Lister & Nutt 1987, Judd & Huey 1984, Mezey 1976, Nuotto et al. 1982, Menon & Kodama 1985, Alkana et al. 1977, Alkana & Malcom 1982). However, most of the suggested remedies have an insignificant effect on the blood level of ethanol or on its metabolic turnover.

On the other hand, a number of reports related to liver function and alcohol metabolism are disclosed as follows. There are:

Pettersson G. (1987), "*Liver alcohol dehydrogenase,*" CRC-Crit-Rev. 21(4) 349–89; Gianoulakis C. (1989), "*The effect of alcohol on the biosynthesis and regulation of opioid peptides,*" Experientia 45(5), 428-35; Hoekn, J.B. et al. (1992), "*Ethanol and signal transduction in the liver,*" FASEB - J. 6 (7), 2386–96; Mitchell MC and Herlong HF (1986), "*Alcohol and nutrition, Caloric Value, bioenergetics and relationship to liver damage,*" Ann. Rev. Nutr. 6(4), 457–74; Gellert J and Teschke, R. (1988), "*The biochemistry of alcohol metabolism,*" Z. Gastroenterol. 26 (suppl 3) 22-7; and *Principles of Biochemistry* (1993), (Lehninger, Nelson, Cox) 3rd ed., Chap. 18, pp. 9542–597, Worth Publishers.

U.S. Pat. No. 5,102,910 discloses a pharmaceutical composition containing (a) L-asparaginic acid, (b) L-cysteine, (c) L-glutaminic acid, (d) sodium selenate, and (e) zinc acetate or zinc sulfate for use as a liver function actuating agent. However, this patent disclosed neither a specific mechanism, nor data in vitro or in vivo.

SUMMARY OF THE INVENTION

Accordingly, it is an object of the present invention to provide a pharmaceutical preparation comprising L-aspartate or L-asparagine for use in adding to foods, food additives, soft drinks, vitamins, or the like so as to prevent ethanol toxicity and a process for the preparation thereof.

Another object of the present invention is to provide a pharmaceutical compound of ASP or ASN as a solid, liquid, or powder preparation for preventing ethanol toxicity and a process for the preparation thereof.

A further object of the present invention is to provide a method of administering 0.001 g to 0.4 g/Kg/day of ASP or ASN to a human for preventing ethanol toxicity.

Still another object of the present invention is to provide a method of administering about 0.001 to 0.4 g/Kg/day of ASP or ASN to a human for reducing, relieving, or preventing liver damage, tissue damage, and change of mental capacity or coordination after the human drinks alcohol.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention.

DESCRIPTION OF PREFERRED EMBODIMENTS

There is provided a pharmaceutical preparation for preventing ethanol toxicity as shown in FIGS. 1 to 7; the pharmaceutical preparation comprising L-aspartate or L-asparagine with a large amount thereof in foods, food additives, soft drinks, vitamins, and a number of types of pharmaceutical preparations. Such pharmaceutical preparations are taken orally, injected or intraperitoneally administered to a human. Injections can be administered to the muscle, hypodermis, or blood.

The compound or composition according to the present invention is provided in the form of granules, tablets, pills, capsules, liquid, powder, etc. for oral administration, and in the form of suspensions, liquids, emulsions, ampules, injections, or combinations thereof for parenteral administration. As a bulk-type for using in a composition, solid, semi-solid, liquid, or powder forms are used. Such compositions include water, soda water, vitamins, salts, soups, meats, amino acids, fruits, crops, vegetables, fish, algae, organic acids, etc. or a combination of two or more of them.

According to the present invention, the ratio of ASP or ASN in the composition is preferably about 0.1–100% by weight, preferably, 0.2–10% by weight. When the composition is in liquid form such as soups, soft drinks, or reconstitutive drinks (e.g. Gatorade ™), it contains 0.1–10.0% by weight, preferably, 0.2–1.0% by weight of ASP or ASN. Also, it simultaneously includes 0–10.0% by weight, preferably 1–5% by weight of other amino acids, sugars such as sucrose, lactose, glucose, oligosaccharides, Steviosides, etc., organic acids or vitamins. It may selectively contain 0–0.1M, preferably 0.02–0.04M, of an electrolyte mixture such as soluble sodium or potassium salts (NaCl, KCl, etc.).

The composition of the present invention, when formulated in a capsule or tablet form, can contain 0.2–90% by weight, preferably, 30–50% by weight of ASP or ASN with the remainder comprising vitamins, amino acids, sugars, organic acids, etc.

Table 1 shows additional optional ingredients to L-aspartate or L-asparagine according to the present invention as below.

TABLE 1

| Additional Optional Ingredient to ASP or ASN | | |
|---|---|---|
| Ingredient | Usual Content | Preferable |
| ASP or ASN | 0.2–100 weight % | 30–50 weight % |
| Amino acids | q.s. | q.s. |
| Artificial spices | q.s. | q.s. |
| Natural spices | q.s. | q.s. |
| Sugars | q.s. | q.s. |
| Vitamins | q.s. | q.s. |
| Pigments | q.s. | q.s. | wherein q.s. is quantum sufficient.

The present invention can prevent, alleviate, or relieve liver damage, other tissue damage, and change of mental capacity or coordination or other intoxication associated behavior in humans caused by consumption of alcohol.

Figure 1:
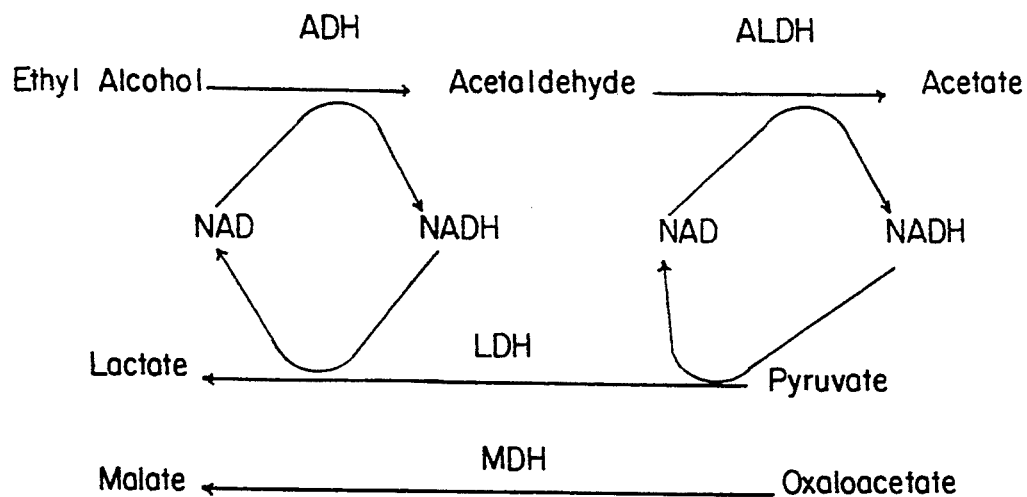
FIG. 1 shows a pathway of metabolic turnover of ethanol according to the present invention.

In general, it is well accepted that ethanol is oxidized to acetaldehyde through three independent metabolic pathways, such as alcohol dehydrogenase (hereinafter "ADH"), the cytochrome P450 system (hereinafter "MEOS"), and catalase. As shown in FIG. 1, the central and major mechanism of ethanol oxidation is the reaction with ADH with NAD as a cofactor. ADH activity is primarily located in the cytosol of hepatocytes, but is also found in other tissues, notably in the gastrointestinal tract. Also, in general, the metabolic turnover of ethanol to acetaldehyde by ADH accompanies the reduction of NAD to reduced nicotinamide adenine dinucleotide (hereinafter "NADH").

Regarding the non-ADH mediated metabolism of ethanol, the relative contributions of catalase and of the MEOS are controversial. Since the cytochrome P450-dependent monooxygenase, oxidizing ethanol and other primary alcohols using nicotinamide adenine dinucleotide phosphate (hereinafter "NADPH") as a cofactor, is inducible and has a higher Km for ethanol, MEOS may play a greater role in chronic alcoholics and at higher concentration of ethanol. In general, recent interest in MEOS is generated by its role in xenobiotic activation of carcinogens and drugs. The other non-ADH ethanol oxidizing activity (by catalase) is dependent on $H_2O_2$ availability and is suggested to have a considerable importance in brain.

The consequent acetaldehyde formed from ethanol is very toxic and should be eliminated immediately, for which acetaldehyde dehydrogenase (hereinafter "ALDH") is solely responsible. For the conversion of acetaldehyde to acetate, the concomitant reduction of NAD is required. Therefore, in the successive metabolic turnover of ethanol to acetate through acetaldehyde, the cellular NAD/NADH status has much importance.

Therefore, ethanol oxidation via ADH and ALDH consumes cytoplasmic NAD and is followed by a decrease in the cellular NAD/NADH ratio. The decreased cytosolic NAD/NADH ratio can cause many biochemical changes and damage in the tissues. Since all the reactions of NAD dependent dehydrogenases in the cytosol are affected, the change of the ratio results in an increase in lactate production, δ-aminolevulinic acid synthesis, increased catabolism of male hormone and acetaldehyde accumulation with the simultaneous decrease in gluconeogenesis, galactose oxidation and citric acid cycle activity, etc.

In addition, ethanol and its metabolites have their own biological effects on liver, brain, and gonads through intracellular signal transduction systems, biosynthesis and degradation of fatty acids and proteins, and direct interaction with several functional proteins. In most cases, these biological effects caused by ethanol are deleterious to the tissue. Therefore, if there were any biochemical means to accelerate the complete oxidation of ethanol to acetate, such means would reduce the intracellular level of ethanol or acetaldehyde and could, either directly or indirectly, prevent many types of cellular damage by ethanol.

The metabolic effects of ethanol are varied, and are derived either directly from ethanol and acetaldehyde or indirectly from the derangement of the cytosolic NAD/NADH ratio in consequence of ethanol oxidation. To maintain cellular homeostasis and to protect cells from alcoholic damage, it is reasonable to one of skill in the art that cells can accelerate the metabolic elimination of ethanol, potentiated by NAD regeneration capacity.

Figure 2:
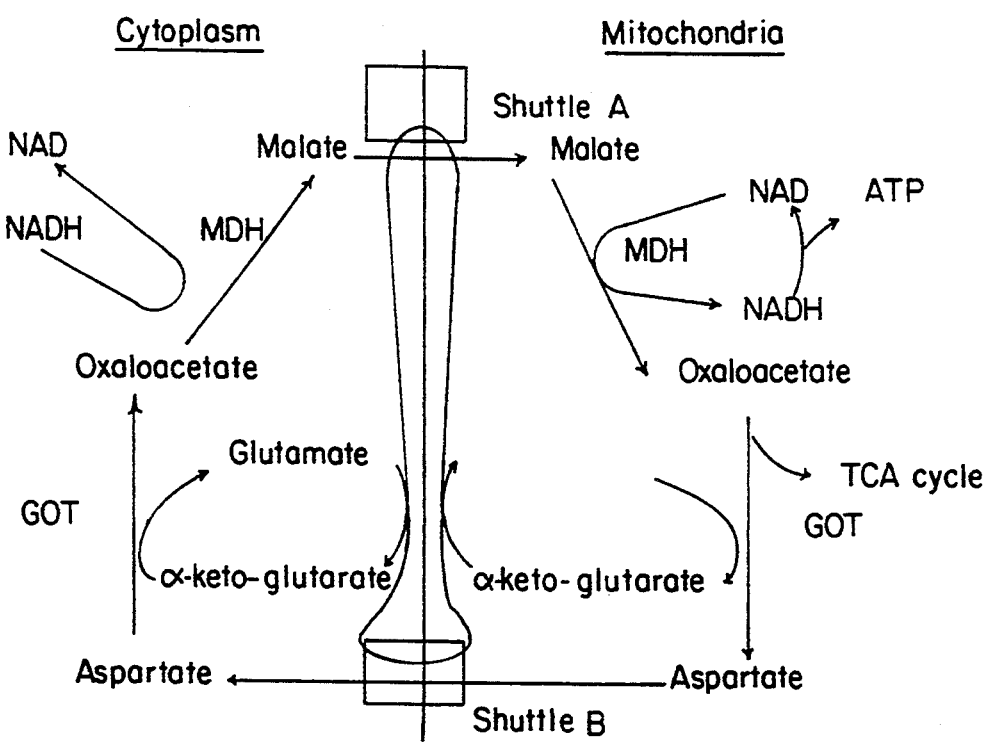
FIG. 2 shows a metabolic regenerating system of cytosolic nicotinamide adenine dinucleotide (hereinafter "NAD") by the malate-aspartate shuttle according to the present invention.

Since most dehydrogenases are NAD dependent, there are a number of NAD regeneration systems. For that purpose, the activation of dehydrogenases by regulatory molecules or by addition of substrates can be tested. In the present invention, the latter aspect of ADH activation by stimulating NAD regeneration was considered. Moreover, the in vivo availability of the substrate from the exogenous route led the present inventors to analyze lactate dehydrogenase (LDH) and malate dehydrogenase (MDH). Though $\alpha$ ketoacids might not enter cells, their precursors such as aspartate or asparagine can be readily absorbed into the cells, which are efficiently transaminated intracellularly to the corresponding $\alpha$ ketoacids (FIG. 2). Pyruvate and oxaloacetate can be reduced to lactate and malate respectively by the specific transaminases with the regeneration of NAD from NADH. In consequence, the recycled NAD can be used for further oxidation of ethanol. All the enzymes involved in this NAD/NADH recycling for ethanol oxidation such as alcohol dehydrogenase (hereinafter "ADH"), lactate dehydrogenase (hereinafter "LDH"), glutamate pyruvate transaminase (hereinafter "GPT"), malate dehydrogenase (hereinafter "MDH"), and glutamate oxaloacetate transaminase (hereinafter "GOT") have the characteristics of working near equilibrium. That is, activity of these enzymes is governed by mass action law and depends on the concentration of substrates. Such a characteristic of equilibrium enzymes has the strong advantage in alleviation of the metabolic turbulence and rapid harmonization of cellular functions without use of energy or complex allosteric regulatory systems.

Figure 3:
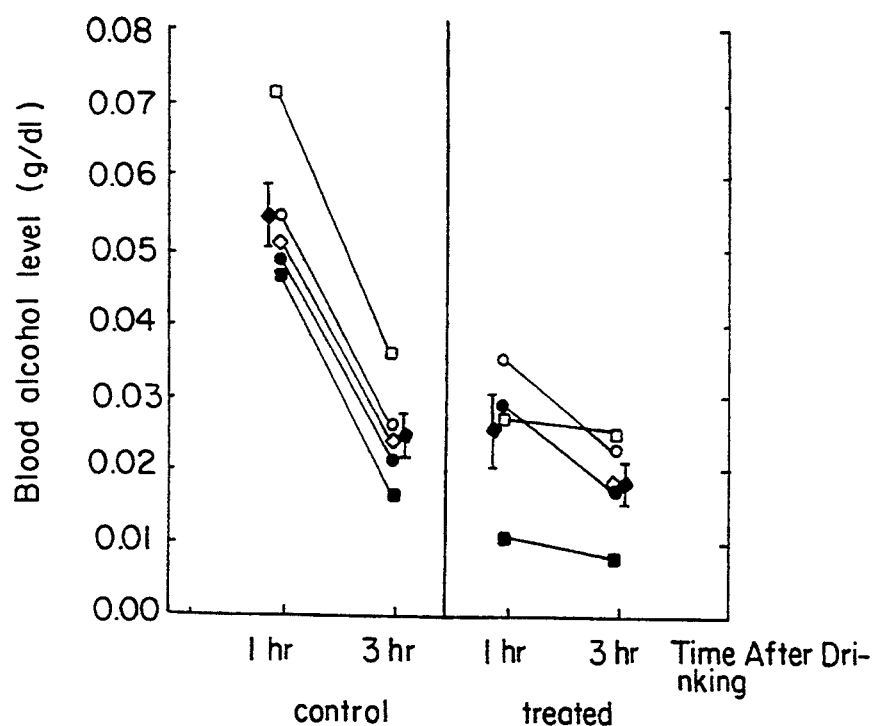
FIG. 3 shows a change in blood alcohol level after ethanol comsumption upon treatment with ASP according to the present invention; levels in untreated control subjects are also shown.
Figure 4:
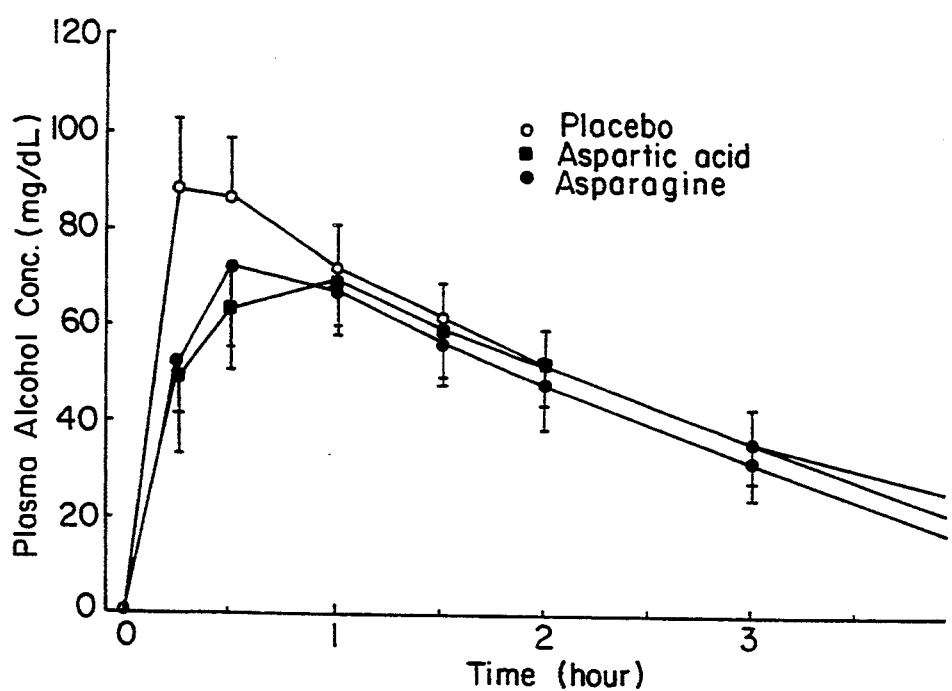
FIG. 4 shows the effect of ASP and ASN on pharmacokinetics of ethanol in a human (blood ethanol level) according to the present invention.
Figure 5:
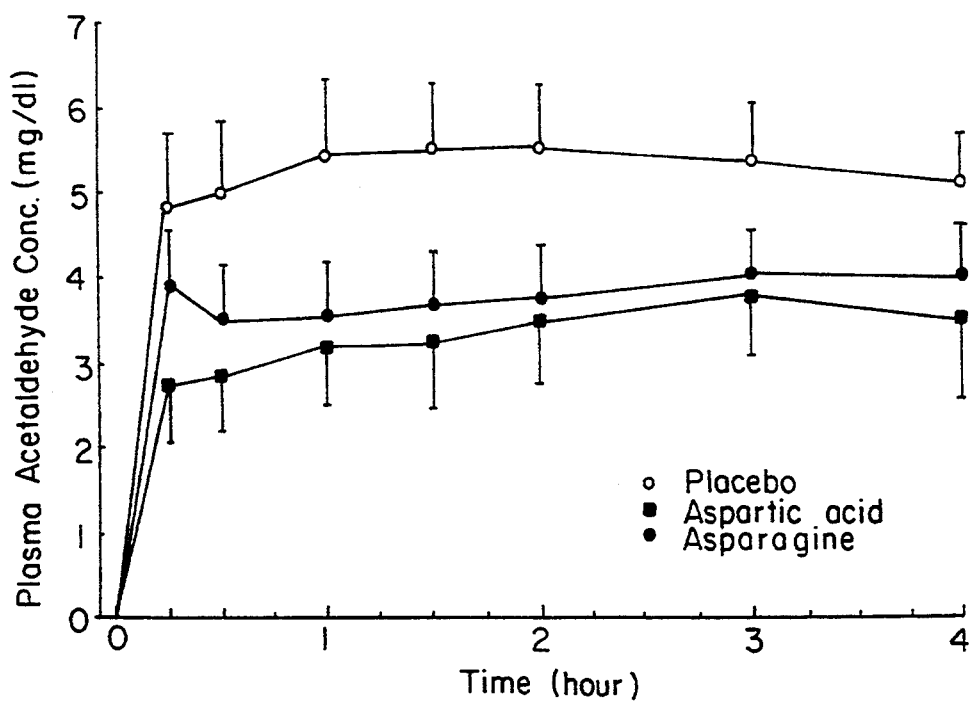
FIG. 5 shows the effect of ASP and ASN on the pharmacokinetics of ethanol in a human according to the present invention.

The stoichiometric recycling of NAD by addition of aspartate or asparagine can be observed either in a GOT/MDH coupled system or in a GPT/LDH coupled system. The double coupled systems of ADH/MDH/GOT enzymes or ADH/LDH/GPT enzymes were also found to operate efficiently in oxidation of ethanol to acetaldehyde. The two systems were almost similar in efficiency, but in the aspect of biological significance, ADH/MDH/GOT system is preferable in the application of in vivo ethanol oxidation. The MDH/GOT coupled system is well balanced between cytosol and mitochondria through the known malate-aspartate shuttle for NAD/NADH transport (FIG. 3). In the mitochondria, transported NADH can be readily used for oxidative phosphorylation, which can reinforce the citric acid cycle activity deranged by ethanol. Therefore, malate, the resulting product of ethanol oxidation by a ADH/MDH/GOT system, can be readily absorbed into mitochondria without any metabolic sequelae. The regenerated NAD from this cycle can accelerate the oxidation of acetaldehyde to acetate by aldehyde dehydrogenase (hereinafter "ALDH"), since ALDH is also NAD-dependent.

Therefore, augmentation of the malate-aspartate shuttle by enrichment of aspartate can facilitate the NAD regeneration cycle, which accelerates the complete oxidation of ethanol to acetate in cells. This mechanism contributes to the lowering of ethanol levels in the tissues after drinking and to the prevention of alcoholic damage either by ethanol and acetaldehyde or by the decreased cellular NAD/NADH ratio. Accordingly, in the present invention, there is developed a method of restoring the ratio of cellular NAD/NADH lowered by the metabolic degradation of alcohol, accelerating the metabolism of alcohol and acetaldehyde, shortening the time they remain in tissues. Consequently, the objects of the invention to prevent or relieve the tissue damage, metabolic disequilibrium caused by the change of NAD/NADH, and prevent, alleviate, or relieve the diseases including liver disease and the mental and behavioral disorder caused by long alcoholism are accomplished. For the adjustment of the ratio of NAD/NADH, the former system between the malate-aspartate shuttle and glycerol phosphate shuttle can be readily supplied via transamination of the corresponding aspartate or asparagine by the abundant respective tissue cytosolic transaminases. That is, because NAD and NADH cannot be transported directly across cell membranes, the adjustment of intracellular NAD and NADH is accomplished by the transportation of $\alpha$-ketoglutarate across the mitochondrial membrane.

In the malate-aspartate shuttle, oxaloacetate cannot diffuse across the mitochondrial membrane and aspartate is stoichiometrically circulated by the glutamate-aspartate transporter and malate-$\alpha$-ketoglutarate transporter. Also, in the cytoplasm, aspartate reacts with $\alpha$-ketoglutarate through the transaminase to produce oxaloacetate and glutamate, and the thus produced oxaloacetate oxidizes NADH to NAD by malate dehydrogenase (hereinafter "MDH") with reduction of the oxaloacetate to malate. This pathway is most important in regenerating NAD exhausted in cytoplasm and malate is taken up into mitochondria and subsequently converted into oxaloacetate or aspartate or used in the Krebs cycle. Because aspartate aminotransferase or MDH used in this pathway exist abundantly in tissues and have equilibrium enzymatic characteristics, the enzymatic reaction rate is mainly adjusted by the large amount of substrate.

In the present invention, the malate-aspartate shuttle was used as a method to supplement NAD exhausted by alcohol metabolism by use of biochemical properties of tissues, and it made easy the conversion of the multi-produced NADH to NAD by improving the MDH activity by raising the concentration of cellular oxaloacetate. But, as oxaloacetate is not easily transported across cell membranes, aspartate is easily converted to oxaloacetate by aspartate aminotransferase existing abundantly in tissue by adding the transportable aspartate, and consequently the concentration of oxaloacetate is raised indirectly. It is clear that the addition of aspartate can accelerate the ethanol oxidation. Also, in the present invention, the addition of asparagine which produces aspartate in the human body produces a similar effect as the addition of aspartate because asparagine absorbs in the intestinal epithelium and is converted to aspartate directly by asparaginase.

In the present invention, blood alcohol level according to the time passed was compared between an alcohol only treated group and an alcohol and aspartate (or asparagine) treated group. The result was that the metabolic conversion of ethanol could be accelerated by augmenting NAD regeneration by treatment with aspartate or asparagine with consequent lowering of the ethanol level. This effect can be applied to the cellular metabolic equilibrium as well as diseases and mental and behavioral disorder caused by alcohol. In a simulatory test by the intraperitoneal injection of an animal, the present invention could obtain a significant effect.

Test Example 1

Drinking Ethanol Test

1. Experimental Materials

Johnny Walker whisky (black label) 86 proof was used as an alcohol and sodium aspartate (manufactured by Tanabe Company in Japan) was used. Healthy persons of age in the early 20's, who have no specific history of illness and particularly have no abnormal symptoms in tests of liver function, were adopted as experimental subjects. Blood alcohol concentration was measured by gas chromatography.

2. Experimental Method

After letting 5 subjects drink 120 ml of whisky (86 proof) individually, blood alcohol levels were measured by gathering 2 ml of blood after 1 hour and 3 hours, respectively. Three days after the first experiment, having let the same persons drink alcohol together with taking a capsule of 5 g of aspartate simultaneously, the blood alcohol level was measured by the same method as above. Also, a concise test of body balance was made in each case 1 hour after drinking. The body balance test was repeated three times. Such body balance test proceeded by having the subject walk straight in one direction, for a distance of 3 meters, with the arms outstretched to the side. Abnormal performance was indicated by a deviation from a straight line path 15 cm wide.

3. Blood alcohol level change by the aspartate administration.

As shown in Table 2 and FIG. 3, compared to the alcohol only treated group, the alcohol and L-aspartate treated group showed the effect that blood alcohol concentration was reduced more than 55% ($P<0.05$) after 1 hour from drinking (to 0.01–0.04 g/dL). After 3 hours, blood alcohol levels in both groups were equal. It can be explained that this effect (the reduction of blood alcohol concentration by the L-aspartate administration) resulted from the acceleration of alcohol metabolism and the subsequently prompt alcohol oxidation caused by the reinforcement of NAD reproductivity through L-aspartate administration as shown in Table 2.

TABLE 2

Blood Alcohol Level Change by Administering ASP After Drinking Alcohol

| Time After Drinking | Alcohol Only Treated Group (5 Person) (g/dl) | Alcohol and ASP Treated Group (4 Person) (g/dl) |
|---|---|---|
| 1 hour | 0.055 ± 0.010 | 0.025 ± 0.010 |
| 3 hours | 0.024 ± 0.007 | 0.018 ± 0.017 | wherein an amount of alcohol administration was 120 ml (86 proof whiskey) and an amount of ASP administration was 5 g powder.

4. Change in the body balance index after drinking by administering ASP.

Analysing the body balance index after 1 hour from administration of alcohol shows that reduction of blood alcohol level by administering aspartate results in improvement of alcohol-induced behavioral disorder (Table 3). While as the error rate was 53% in the alcohol only treatment group, it was only 26% in the alcohol and aspartate treatment group. That is, it showed a 49% improvement of body balance as shown in Table 3.

TABLE 3

Effect of Body Balance Index by Administering ASP after Alcohol Drinking

| Experiment Group | Alcohol Only Treated Group | Alcohol and ASP Treated Group |
|---|---|---|
| Body balance error ratio | 8/15 (53%) | 4/15 (26%) |

Test Example 2

Intraperitoneal Alcohol Injection

1. Experimental Materials and Method

Sprague-Dawley white rats weighing 200 g were used in the experiment. All the reagents used in the present experiment were analytical grade. L-aspartate was a product manufactured by Tanabe Company in Japan and was used by solubilizing to the appropriate concentration in sterile water, adjusting acidity to pH 7.4 and filtering.

Alcohol injection was intraperitoneal. The rats were divided into five groups of five rats each. The first group was an untreated control. Three of the remaining groups received 2 ml of 50% ethanol. One of the ethanol treated groups received no additional treatment (ethanol only), a second ethanol treated group was treated with a low amount of aspartate (0.75 ml of 0.45M ASP), the third ethanol treated group received a high amount of aspartate (2 ml of 3.45M ASP). The fifth group of rats was treated only with the large amount of aspartate. Each group was treated once a day for five days. On the 6th day the physical conditions of the mice was examined, then they were sacrificed. The liver tissue was extracted and a pathological and histological examination was performed.

2. Aspartate administration ameliorates effects of intraperitoneal alcohol injection.

ASP inhibits inflammation caused by direct intraperitoneal alcohol injection observed histologically (Table 4). Abdominal inflammation and adherence of the tissues in the abdominal cavity was observed in mice receiving only alcohol. These effects were markedly reduced in animals receiving ASP or ASN in addition to alcohol.

TABLE 4

Effect of ASP Administration on Symptoms Resulting from Intraperitoneal Alcohol Injection

| Groups | Adhesion | Liver Inflammation |
|---|---|---|
| Control | − | − |
| Alc. only Treated | +++ | +++ |
| Alc. & low ASP | ++ | + |
| Alc. & high ASP | + | + |
| High ASP only | + | − |

Test Example 3

The Influence on alcohol metabolism of L-aspartate and asparagine administration.

1. Materials and Method

For testing the influence of L-aspartate or asparagine administration on alcohol metabolism in humans, the change of blood alcohol concentration and blood acetaldehyde concentration over time was tested after 120 ml of whiskey (86 proof) and 5 g of L-aspartate or asparagine, respectively, were administered to six healthy adult men. 1 ml of blood was gathered, through a heparin treated catheter, each hour into a vial containing EDTA. Alcohol and acetaldehyde concentration in the blood was measured by gas chromatography on the next day.

2. Results

L-aspartate reduced the blood acetaldehyde concentration by more than 36%; asparagine by more than 30%. This result is statistically significant. Therefore, this shows that the administration of L-aspartate or asparagine is useful in prevention of alcohol toxicity (as shown in Table 5 and FIGS. 4 and 5).

TABLE 5

Effect of Aspartate and Asparagine Administration on Alcohol Metabolism

| Groups | Aspartate Treated Group | Asparagine Treated Group |
| --- | --- | --- |
| Reduction of blood alcohol level | −10.79% | −14.65% |
| Reduction of blood acetaldehyde level | −36.14% | −30.16% |

(percentage of alcohol only controls)

Example 4

Effect of Aspartate and Asparagine on alcohol toxicity to a cell line.

1. Materials and method.

The MTT test was done to analyze the effect of alcohol administration on human cells in vitro, and the effect on alcohol toxicity of aspartate or asparagine. The mammalian hepatoma cell line FT02B was cultured in a medium wherein DMEM was mixed with Ham's F12 medium in equal amounts and 5% calf serum and fetal bovine serum were added. Cells were incubated 5% $CO_2$ and 95% air at 37° C. Cells were distributed into a 96 well plate at $5 \times 10^3$ cells per well. Alcohol, or alcohol plus aspartate, or alcohol plus asparagine, at various concentrations of each, was added to the wells. After 4 days in culture, absorbance was measured at 540 nm with a ELISA plate reader to count the number of surviving cells by use of the coloring reaction induced by addition of MTT (C3-4,5-dimethyl-thiazol-2yl)-2,5 diphenyltetrazolium bromide) and dimethylsulfoxide. $IC_{50}$ as an index of cell toxicity under each condition (alcohol, alcohol plus ASP, alcohol plus ASN) was deteremined by the concentration of alcohol providing 50% cell survival compared to a no alcohol, no ASP (or ASN) control culture.

2. Results of Experimental Test

Figure 6:
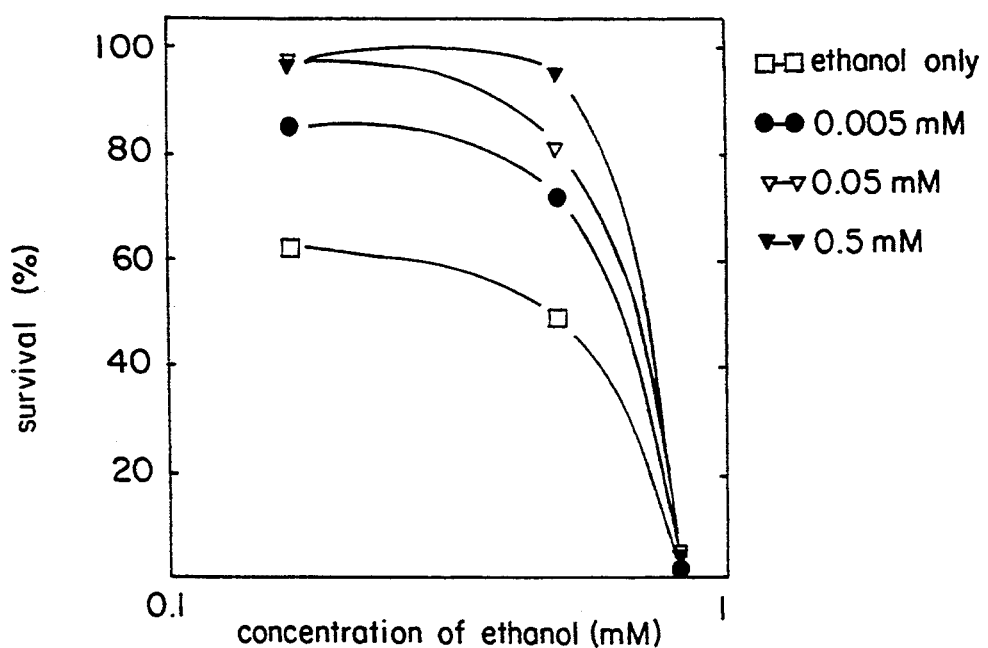
FIG. 6 shows resistance to ethanol toxicity conferred by ASP in human hepatoma cells according to the present invention; ASP was added at 0.005, 0.05 or 0.5 mM.
Figure 7:
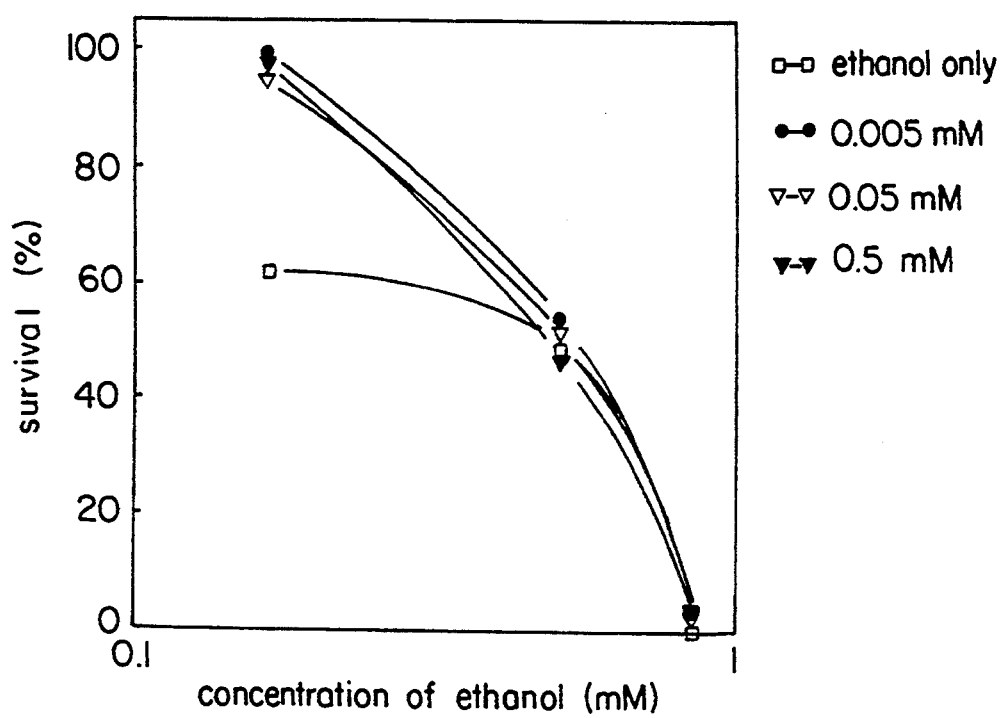
FIG. 7 shows resistance to ethanol toxicity conferred by ASN in human hepatoma cells according to the present invention; ASN was added at 0.005, 0.05 or 0.5 mM.

Aspartate showed dose-dependent amelioration of cytotoxicity of alcohol. Asparagine also showed such effect, though less strongly than aspartate (FIGS. 6 and 7).

Examples of preparations wherein aspartate and asparagine is added to foods, beverages, or vitamins, etc. or used separately with such are as follows:

Preparation Example 1

Aspartate or asparagine was dissolved in soft drinks such as Coca-Cola at 0.2–5 weight % of the amino acid.

Preparation Example 2

Aspartate or asparagine was dissolved in sports drinks such as Gatorade TM at 0.2–5 weight % of the amino acid.

Preparation Example 3

Aspartate or asparagine was added to juice prepared from vegetables such as asparagus, bean sprout, and the juice or extract of fruits such as pear, peach, apple at 0.5–1.5 weight % of the amino acid.

Preparation Example 4

Aspartate or asparagine was added to or mixed with crude vitamins so as to be prepared in the form of tablet or capsules.

Preparation Example 5

Aspartate or asparagine was mixed with one or two additional amino acids, citric acids, or sugars so as to be prepared in the form of a tablet or capsule wherein the aspartate or asparagine is present at 0.1 to 90%, preferably 0.1–50%, most preferably 0.1% to 10% by weight.

Preparation Example 6

Aspartate or asparagine was mixed with one or two additional amino acids or with vitamins, to be made into solution at 0.5–5 weight % of ASP or ASN, and was prepared for intravenous injection.

Preparation Example 7

Dried fish such as squid, dried pollack, or the like, was soaked in a solution 10–90 weight % of flavored aspartate or asparagine solution and dried to be used for relish.

Preparation Example 8

In preparation of snacks such as crackers, aspartate or asparagine was added or mixed at 0.1–10 weight % compared to flour weight, and oil fried to prepare snacks.

The invention being thus described, it will be obvious that the same may be varied in many ways. Such variations are not to be regarded as a departure from the spirit and scope of the invention, and all such modifications as would be obvious to one skilled in the art are intended to be included within the scope of the invention as described by the following claims.

What is claimed is:

1. A method for reducing blood alcohol concentration in a human subject, who has consumed ethanol in a quantity sufficient to elevate their blood alcohol concentration, which comprises administering a pharmaceutical composition containing at least 30% by weight of L-aspartate or L-asparagine to said human subject in an amount effective to reduce said blood alcohol concentration, the amount of L-aspartate or L-asparagine ranging from 0.001 to 0.4 g/kg/day.

2. The method of claim 1, wherein said amount ranges from 0.01 to 0.4 g/kg/day.

3. The method of claim 1, wherein the L-aspartate or L-asparagine is injected into a human tissue selected from the group consisting of muscle, hypodermis, and blood.

4. The method of claim 1, wherein said L-aspartate or L-asparagine is mixed with a food, drink, juice, or other beverage.

5. A method in accordance with claim 1, wherein the subject drinking alcohol is administered a pharmaceutical composition consisting essentially of an amino acid, said amino acid being L-aspartic acid or L-aeparagine, wherein said amino acid is present in the composition in an amount ranging from 30–50% by weight of said composition, and a pharmaceutically acceptable carrier or diluent.

6. The method of claim 5, wherein said L-aspartate or L-asparagine is admixed with additional compounds selected from the group consisting of water, vitamins, sugars, salts, amino acids and organic acids.

* * * * *